United States Patent [19]
Staples

[11] Patent Number: 6,102,698
[45] Date of Patent: Aug. 15, 2000

[54] ORTHOGNATHIC SURGERY SIMULATION INSTRUMENT

[76] Inventor: Ronald C Staples, 4250 Faronia Rd., Memphis, Tenn. 38116

[21] Appl. No.: 09/270,495

[22] Filed: Mar. 15, 1999

[51] Int. Cl.[7] .................................................. A61C 11/00
[52] U.S. Cl. .............................. 433/75; 433/56; 433/57
[58] Field of Search ................................ 433/75, 54, 55, 433/56, 57, 61, 62

[56] References Cited

U.S. PATENT DOCUMENTS

| | | |
|---|---|---|
| 4,047,302 | 9/1977 | Cheythey . |
| 4,758,155 | 7/1988 | Marino ........................................ 433/54 |
| 4,762,490 | 8/1988 | Ludwigs .................................... 433/56 |
| 5,281,135 | 1/1994 | Schwestka-Polly ....................... 433/56 |

*Primary Examiner*—Ralph A. Lewis
*Attorney, Agent, or Firm*—Michael I. Kroll

[57] ABSTRACT

An oral surgery simulating device for planning an oral surgery for a patient including a stand having a base, a device for receiving a cast of a mandible of the patient movably connected to the base, a device for receiving a cast of a maxilla of the patient connected to the stand and positioned atop the cast of the mandible and a pointing unit releasably connected to the stand for aligning the cast of the mandible and the cast of the maxilla with relation to Frankfort's horizontal plane to thereby provide a replica of an upper and lower jaw of the patient. The device for receiving the cast of the maxilla is adjustable in a lateral direction and rotatable. The pointer unit includes a pole, a C-shaped clamp connected to and slideable along a length of the pole and first, second and third pointers extending from the C-shaped clamp for measuring the upper and lower jaw of the patient in relation to Frankfort's horizontal plane. The device for receiving the mandible includes an adjusting device for positioning the cast of the mandible replicating the lower jaw of the patient. The device for receiving the maxilla also includes an adjusting device for positioning the cast of the mandible in a position replicating the upper jaw of the patient. A mandibular ramus facsimile is also pivotally connected to the stand for simulating the ramus of the patient.

36 Claims, 7 Drawing Sheets

ORTHOGNATHIC SURGERY SIMULATION INSTRUMENT

BACKGROUND OF THE INVENTION

1. Field of the Invention

The present invention relates generally to equipment for simulating oral surgery and, more specifically, to a device for aiding a surgeon in planning surgical cuts and procedures prior to oral surgery whereby the device is able to simulate the structure and movement of the condyle, ramus, mandible and maxilla of the patient using a cast and measurements taken from the patient to provide a model on which the surgeon can plan the operation.

2. Description of the Prior Art

Prior art devices for simulating the structure and movement of the upper and lower jaw bones of a patient were unable to adequately provide exact movement and relationships between the bones. Such devices used a one point method of determining the relationship between the maxilla and mandible and therefore only accounted for under and overbite situations. These devices did not account for the sideways alignment of the maxilla and mandible. Furthermore, these devices are only able to align casts of the maxilla and mandible along a single point. Preparation of these devices for simulation required a large amount of time as did the examination of the structure of the maxilla and mandible in order to plan the subsequent surgery. While these units may be suitable for the particular purpose to which they address, they would not be as suitable for the purposes of the present invention as heretofore described.

It is thus desirable to provide an oral surgery simulating device wherein the casts of the maxilla and mandible may be secured thereto and be rotated axially as well as laterally and longitudinally to provide a realistic model of the movement of the bones of the patient. It is further desirable to provide an oral surgery simulating device able to take measurements relative to Frankfurt's horizontal plane and transferring the measurements to the device to provide a proper alignment of the maxilla and mandible casts of the patient in both the longitudinal and lateral directions. It is still further desirable to provide an oral surgery simulating device including a pointer having three adjustable measuring points for accurately taking the desired measurements in three different areas. It is even further desirable to provide an oral surgery simulating device able to provide a mandibular ramus facsimile which is adjustable to provide posterior, anterior, superior and inferior movement. It is still further desirable to provide an oral surgery simulating device able to reduce the preparation time necessary for planning surgery.

SUMMARY OF THE PRESENT INVENTION

The present invention relates generally to equipment for simulating oral surgery and, more specifically, to a device for aiding a surgeon in planning surgical cuts and procedures prior to oral surgery whereby the device is able to simulate the structure and movement of the condyle, ramus, mandible and maxilla of the patient using a cast and measurements taken from the patient to provide a model on which the surgeon can plan the operation.

A primary object of the present invention is to provide an oral surgery simulating device that will overcome the shortcomings of prior art devices.

Another object of the present invention is to provide an oral surgery simulating device which is able to accurately provide a model of the maxilla and mandible of a patient.

A further object of the present invention is to provide an oral surgery simulating device which is able to provide posterior, anterior, superior and inferior movement of the casts of the maxilla and mandible.

A yet further object of the present invention is to provide an oral surgery simulating device wherein the casts of the maxilla and mandible are able to be rotated.

A still further object of the present invention is to provide an oral surgery simulating device including a pointer device able to be adjusted for taking measurements of the maxilla and mandible relative to Frankfurt's horizontal plane and thus provide for accurate alignment of the casts of the maxilla and mandible.

A further object of the present invention is to provide an oral surgery simulating device having a universal mandibular ramus facsimile for use in simulating a sagittal split of the mandibular ramus.

A further object of the present invention is to provide an oral surgery simulating device wherein the device is able to provide a replica of the upper and lower jaws of a patient for aiding in the planning of oral surgery by a surgeon.

Another object of the present invention is to provide an oral surgery simulating device able to reduce the amount of time needed for preparation of the oral surgery and provide the surgeon with a more accurate plan regarding the necessary steps to perform during surgery.

A still further object of the present invention is to provide an oral surgery simulating device that is simple and easy to use.

An even further object of the present invention is to provide an oral surgery simulating device that is economical in cost to manufacture.

Additional objects of the present invention will appear as the description proceeds.

An oral surgery simulating device for planning an oral surgery for a patient is disclosed by the present invention. The oral surgery simulating device includes a stand including a base, a device for receiving a cast of a mandible of the patient movably connected to the base of the stand, a device for receiving a cast of a maxilla of the patient connected to the stand and positioned atop the cast of the mandible and a pointing unit releasably connected to the stand for aligning the cast of the mandible and the cast of the maxilla with relation to Frankfort's horizontal plane to thereby provide a replica of an upper and lower jaw of the patient. The device for receiving the cast of the maxilla is adjustable in a lateral direction and rotatable about an axis. The pointer unit includes a pole, a C-shaped clamp connected to and slideable along a length of the pole and first, second and third pointers extending from the C-shaped clamp for measuring the upper and lower jaw of the patient in relation to Frankfort's horizontal plane. The device for receiving the mandible includes an adjusting device which based upon measurements taken by the pointer unit is able to position the cast of the mandible in a position replicating the lower jaw of the patient. The device for receiving the maxilla also includes an adjusting device which based upon measurements taken by the pointer unit and the positioning of the cast of the mandible is able to position the cast of the mandible in a position replicating the upper jaw of the patient. A mandibular ramus facsimile is also pivotally connected to the stand for simulating the ramus of the patient.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DETAILED DESCRIPTION OF THE PREFERRED EMBODIMENT

Figure 1:
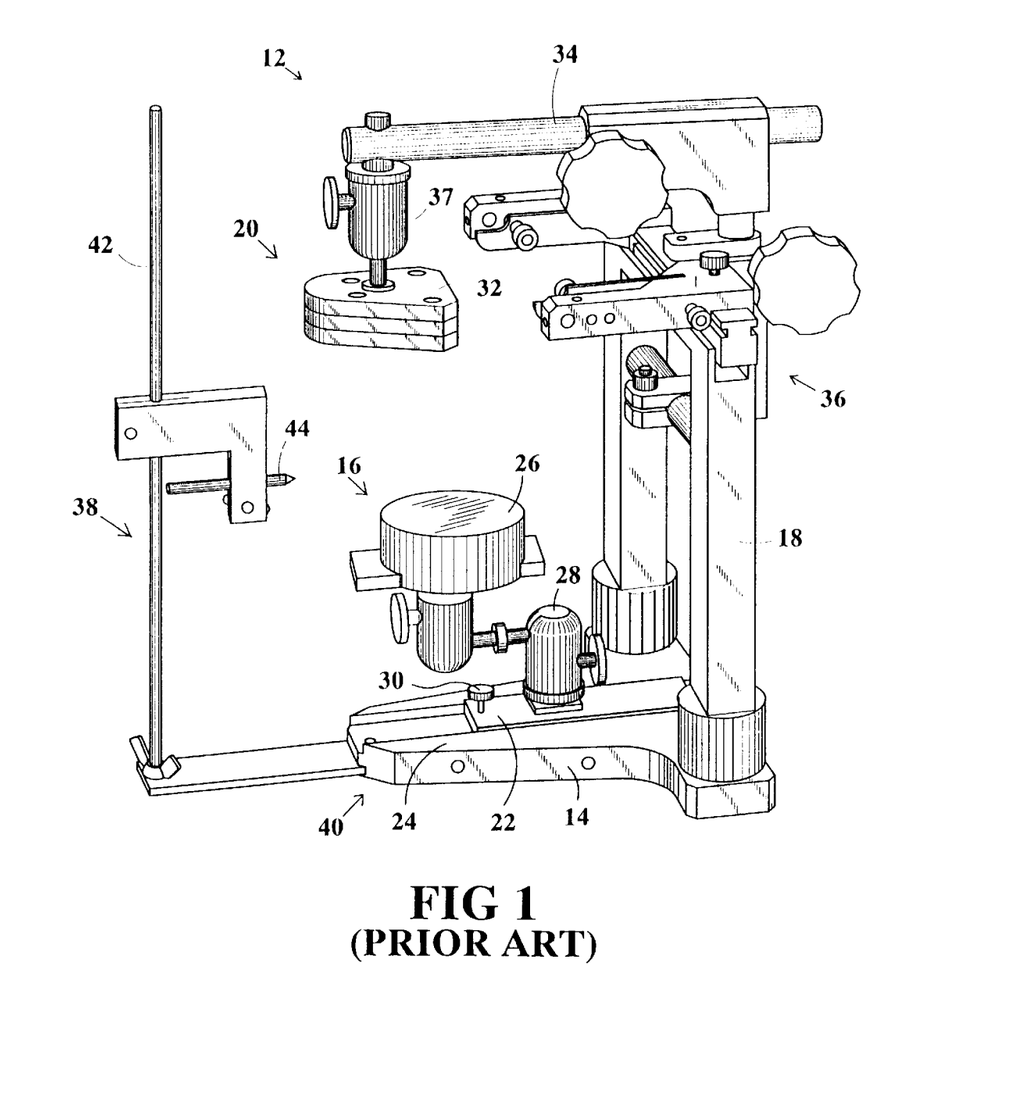
FIG. 1 is a side elevational perspective view of a prior art oral surgery simulating device.

Turning now descriptively to the drawings, in which similar reference characters denote similar elements throughout the several views, FIG. 1 illustrates a prior art oral surgery simulating device 12. The oral surgery simulating device 12 includes a base 14. Extending from the base 14 is a mandibular unit 16 and a stand 18. The stand 18 includes a maxillary unit 20 extending therefrom and positioned above the mandibular unit 16.

The mandibular unit 16 includes a laterally adjustable rod 22 connected to a top side 24 of the base 14, a mandibular plate 26 for securing a cast of the mandible of the patient thereto and an adjustment device 28 connected between the adjustable rod 22 and the mandibular plate 26 for laterally adjusting the mandibular plate 26 more precisely than the adjustable rod 22. The adjustable rod 22 includes a locking mechanism 30 for preventing lateral movement once aligned.

The maxillary unit 20 includes a maxillary plate 32, a lateral adjustment rod 34 for adjusting the maxillary plate 32 in the lateral direction and a longitudinal adjustment device 36 for adjusting the maxillary plate 32 in the longitudinal direction. The cast of the maxilla of the patient is secured to the maxillary plate 32. The maxillary plate 32 is then adjusted using the longitudinal adjustment rod 34 and the lateral adjustment device 36 to align the cast of the maxilla with the cast of the mandible of the patient. A vertical adjustment device 37 is provided for vertically aligning the maxillary plate 32 with the mandibular plate 26.

Slideably connected to extend from the base 14 is a pointer unit 38. The pointer unit 38 is releasably connected to extend from a bottom side 40 of the base 14 and is movable in the lateral direction. The pointer unit 38 is removed from its position connected to the base 14 in order to take a point measurement from a patient for use in aligning the cast of the maxilla and mandible on the oral surgery simulating device. The pointer unit 38 includes a vertically extending pole 42 and a pointer 44 extending therefrom. The pointer 44 extends perpendicular to the pole 42 and is moveable therealong. The pointer 44 is also moveable in the lateral direction. The pointer 44 is used to measure the lateral position of the maxilla with respect to the mandible of the patient and thus aid in aligning the casts thereof on the oral surgery simulating device 10. The single pointer 44 is only able to measure the lateral displacement of the maxilla with respect to the mandible and thus is unable to account for left and right side displacement of the maxilla and mandible. Furthermore, the maxillary unit 20 is unable to provide axial displacement of the maxillary plate 32 and thus cannot account for axial displacement of the maxilla from the mandible of the patient.

Figure 2:
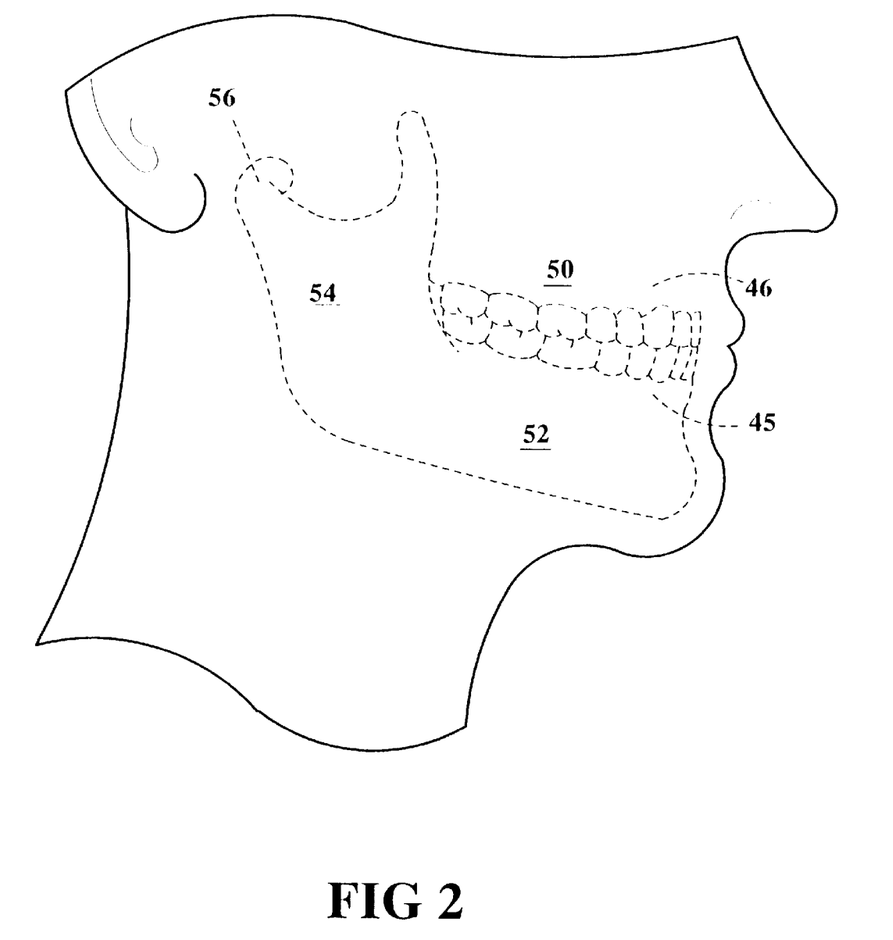
FIG. 2 is a diagrammatic view of the upper and lower jaw of a patient.

A side view of the upper jaw 46 and lower jaw 48 of a person is illustrated in FIG. 2. From this view the maxilla 50 and mandible 52 can be seen in a desired positional relationship. Also illustrated is the ramus 54 which extends from the mandible 52 and the condyle 56. The condyle 56 provides a pivotal connection for the ramus 54 and thus allows the mandible 52 to pivot such as when talking or chewing. The mandible 52 and maxilla 50 illustrated in this figure are properly aligned and thus do not require surgery. The oral surgery simulating device 10 of the present invention is used to align the mandible and maxilla when not in proper alignment such as in the case of a severe overbite. Such surgery will align the maxilla and mandible as illustrated.

FIGS. 3 and 6 through 9 illustrate the oral surgery simulating device of the present invention indicated generally by the numeral 10. The oral surgery simulating device 10 includes a base 58. Extending from the base 58 is a mandibular unit 60 and a stand 62. The stand 62 includes a maxillary unit 64 extending therefrom and positioned above the mandibular unit 60. Also pivotally connected to the stand 62 is a mandibular ramus facsimile 66.

Figure 3:
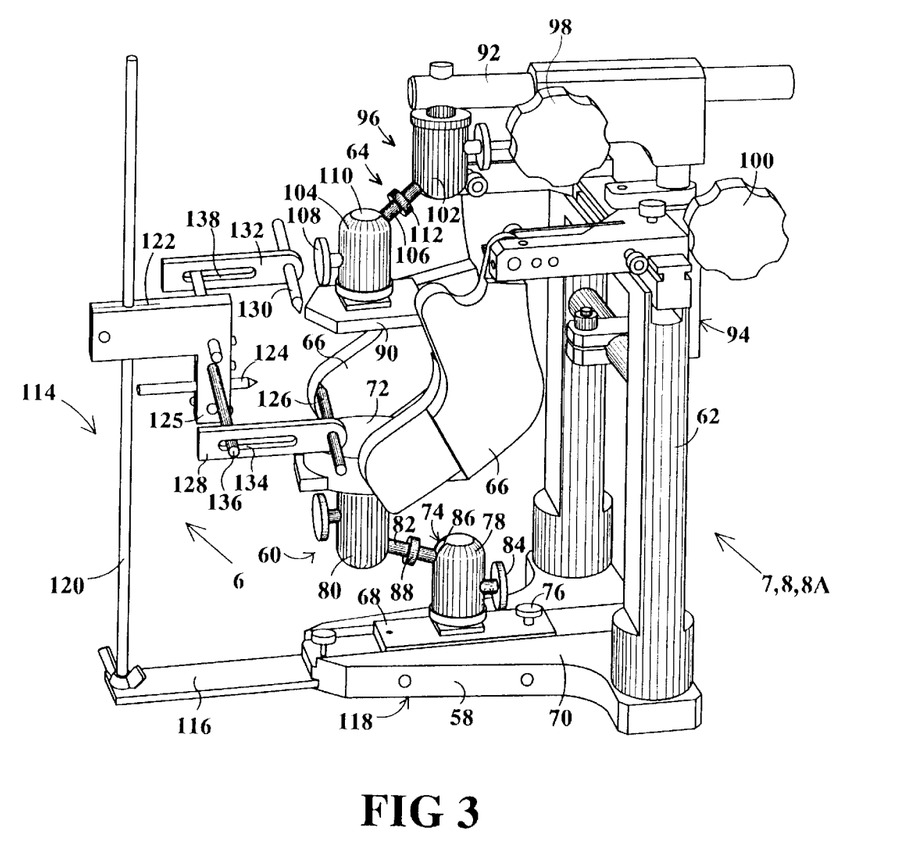
FIG. 3 is a side elevational perspective view of the oral surgery simulating device of the present invention.

The mandibular unit 60 includes a laterally adjustable rod 68 connected to a top side 70 of the base 58, a mandibular plate 72 to which a cast of the mandible of the patient is secured and an adjustment device 74 connected between the adjustable rod 68 and the mandibular plate 72 for more finely adjusting the mandibular plate 72. The adjustable rod 58 includes a locking mechanism 76 for preventing lateral movement once aligned.

The adjustment device 74 provides for finely adjusting the mandibular plate 72 and includes first and second adjusters 78 and 80, respectively, connected together by a diagonally extending bar 82. The first adjuster 78 includes a knob 84 and a slot 86 through which the diagonal bar 82 extends. The knob 84 adjusts the position of the diagonal bar 82 within the slot 86 and thus causes the second adjuster 80 to pivot about the first adjuster 78. A grip 88 is positioned about the diagonal bar 82, whereby the grip 88 causes the second adjuster 80 to be adjusted in the diagonal direction along the diagonal bar 82 when turned. Movement of the second adjuster 80 causes the mandibular plate 72 to move therewith.

The maxillary unit 64 includes a maxillary plate 90, a lateral adjustment rod 92 for adjusting the maxillary plate 90 in the lateral direction and a longitudinal adjustment device 94 for adjusting the maxillary plate 90 in the longitudinal direction. Connected between the maxillary plate 90 and the lateral adjustment rod 92 is a maxillary adjustment device 96. The cast of the maxilla of the patient is secured to the maxillary plate 90. The maxillary plate 90 is then adjusted using the lateral adjustment rod 92 and the longitudinal adjustment device 94 to align the cast of the maxilla with the cast of the mandible of the patient. The lateral adjustment rod 92 includes a knob 98 connected thereto for controlling the lateral movement of the rod 92 and thus of the maxillary unit 90. A knob 100 is connected to the longitudinal adjustment device 94 for controlling the longitudinal movement of the maxillary unit 90.

Figure 7:
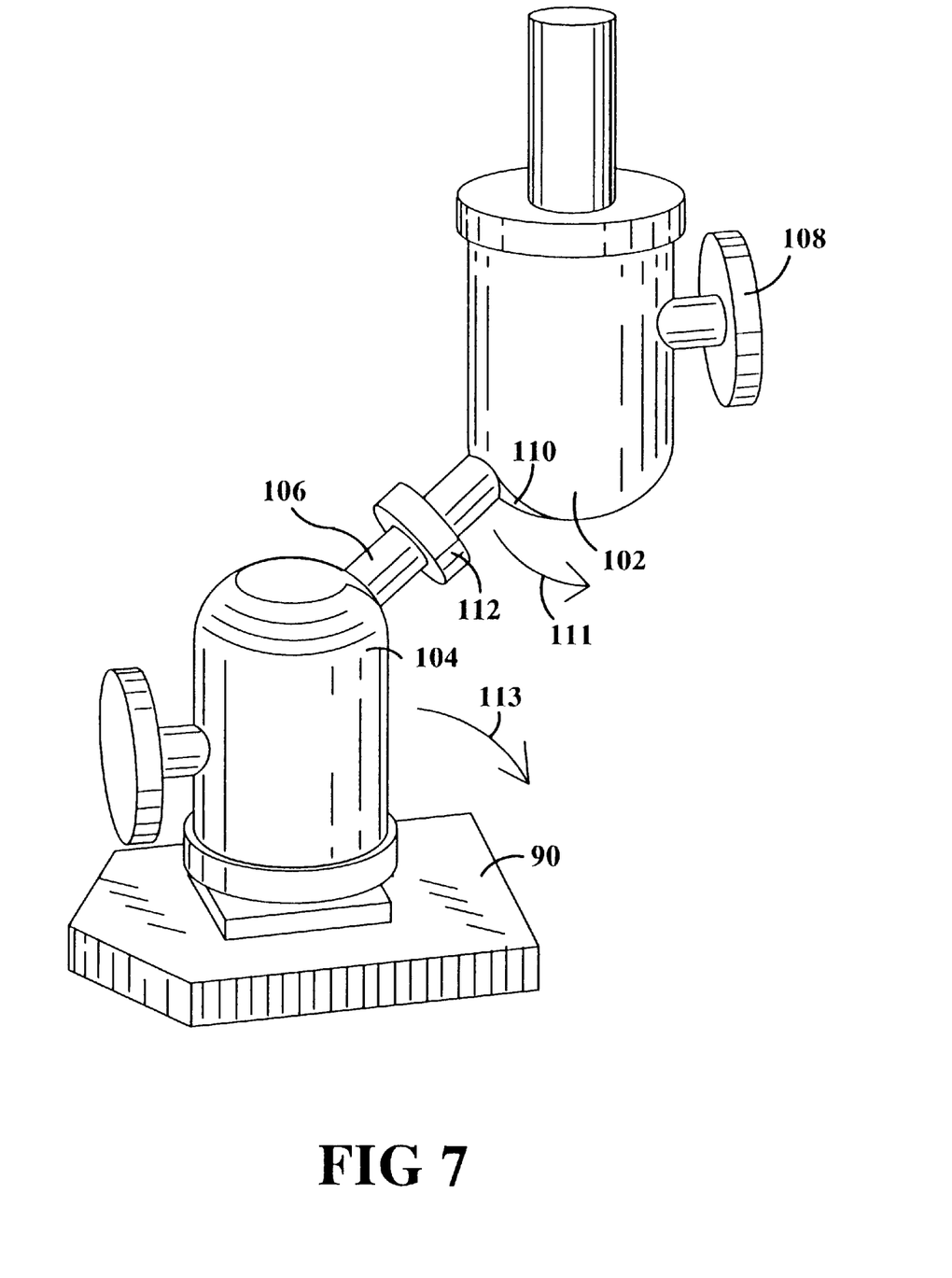
FIG. 7 is a side perspective view of the maxillary unit of the oral surgery simulating device of the present invention, illustrating the rotation of the maxillary unit.

The adjustment device 96 of the maxillary unit 90 is also illustrated in FIG. 7 and provides for finely adjusting the maxillary plate 90 and includes third and fourth adjusters 102 and 104, respectively, connected together by a diagonally extending bar 106. The third adjuster 102 includes a knob 108 and a slot 110 through which the diagonal bar 106 extends. The knob 108 adjusts the position of the diagonal bar 106 within the slot 110 and thus causes the diagonal bar 106 to pivot in the direction of the arrow labeled 111 and the fourth adjuster 104 to pivot about an end of the diagonal bar 106 in the direction of the arrow labeled 113. A grip 112 is positioned about the diagonal bar 106 and, when turned, adjusts the distance at which the diagonal bar 106 extends from the third adjuster 102 thus causing the fourth adjuster 104 to be moved in a diagonal direction. Movement of the fourth adjuster 104 causes the maxillary plate 90 and thus the cast of the maxilla to move therewith.

Figure 6:
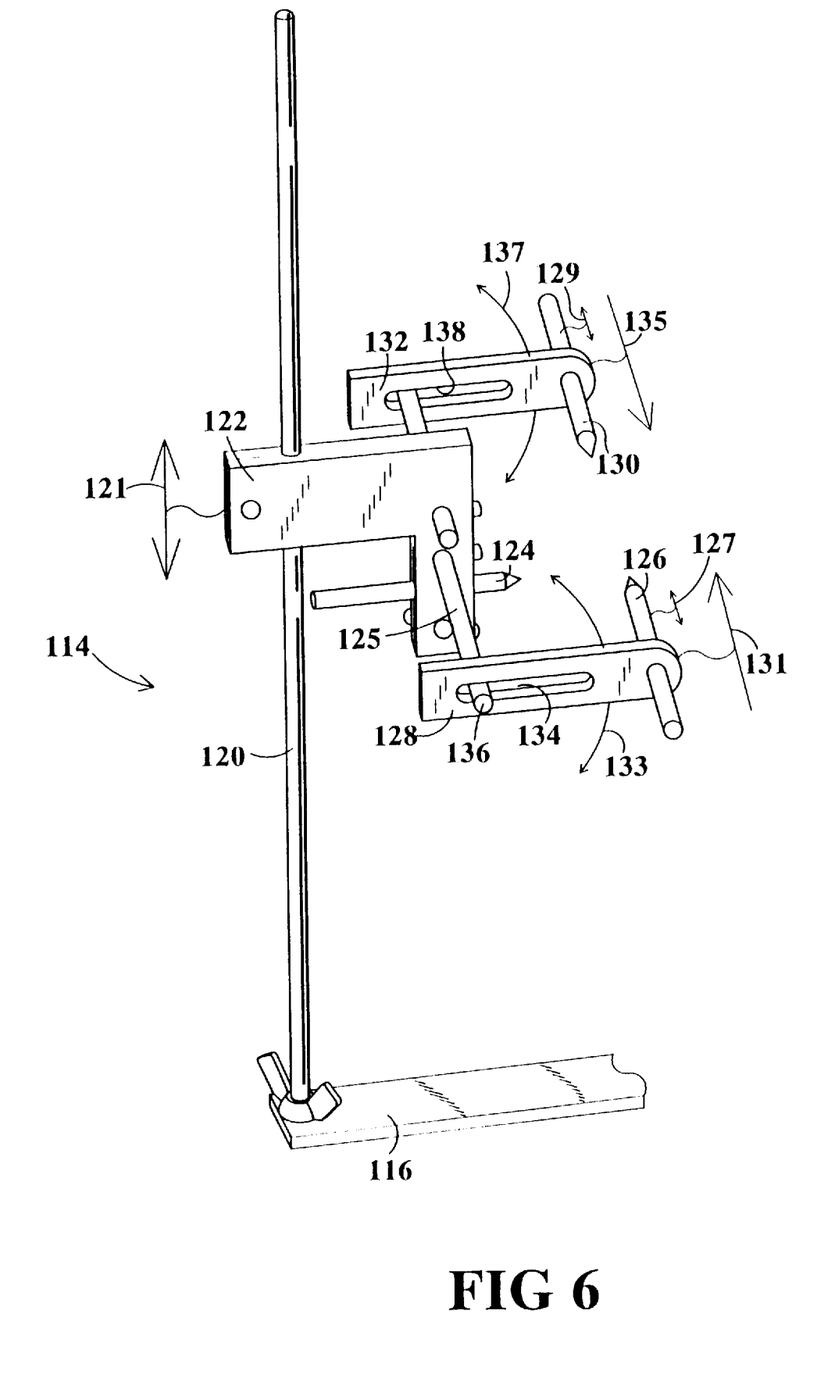
FIG. 6 is a side perspective view of a pointer of the oral surgery simulating device of the present invention.

Slideably connected to extend from the base 58 is a pointer unit 114. The pointer unit 114 is also shown in FIG. 6 and includes a base side 116 which is releasably received by and extends from a bottom side 118 of the base 58. The base side 116 is movable in the lateral direction. The pointer unit 114 is removed from its position connected to the base 58 in order to take measurements from a patient. The measurements are used in aligning the cast of the maxilla and mandible on the oral surgery simulating device 10. The pointer unit 114 includes a vertically extending pole 120 and a pointer clamp 122 extending therefrom and directed towards the base 58 of the oral surgery simulating device 10. The pointer clamp 122 is substantially C-shaped and extends perpendicular to the pole 120. The pointer clamp 122 is moveable along the length of the pole 120 as indicated by the arrow labeled 121. The pointer clamp 122 includes a first pointer 124 extending from a central portion of a midsection 125 of the C-shaped clamp 122 and towards the base 58 of the oral surgery simulating device 10. A second pointer 126 is positioned to extend from a first leg 128 of the C-shaped pointer clamp 122 and towards the first pointer 124. The second pointer 126 is moveable in the direction indicated by the arrow labeled 127. A third pointer 130 is positioned to extend from a second leg 132 of the C-shaped pointer clamp 122 and towards the first pointer 124. The third pointer 130 is moveable in the direction indicated by the arrow labeled 129. The second and third pointers 126 and 130 therefore point towards each other. The first leg 128 includes a slit 134 extending along a length thereof through which a first end 136 of the midsection 125 of the clamp 122 extends. The first leg 128 is movable in the lateral direction, the movement being defined by the length of the slit 134. The first leg 128 is also moveable in a longitudinal direction along the length of the midsection 125 as indicated by the arrow labeled 131 and pivotally about the midsection 125 as indicated by the arrow labeled 133. The second leg 132 also includes a slit 138 extending along a length thereof through which a second end of the midsection 125 of the clamp 122 extends. The second leg 132 is movable in the lateral direction, the movement being defined by the length of the slit 138. The second leg 132 is also moveable in a longitudinal direction along the length of the midsection 125 as indicated by the arrow labeled 135 and pivotally about the midsection 125 as indicated by the arrow labeled 137. The pointer 114 is used to measure the position of the maxilla with respect to the mandible of the patient and thus aid in aligning the casts thereof on the oral surgery simulating device. The use of the first, second and third pointers 124, 126 and 130 allows for the measurements of the position of the maxilla and mandible to be taken along a plane instead of simply at one point as in the prior art. These measurements allow the user to more accurately align the cast of the maxilla with respect to the cast of the mandible by accounting for both lateral and longitudinal (left and right) displacement.

Figure 8:
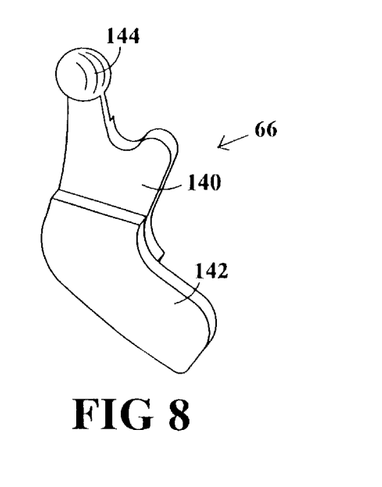
FIG. 8 is a side perspective view of the right mandibular ramus facsimile in the closed position of the oral surgery simulating device of the present invention.
Figure 8A:
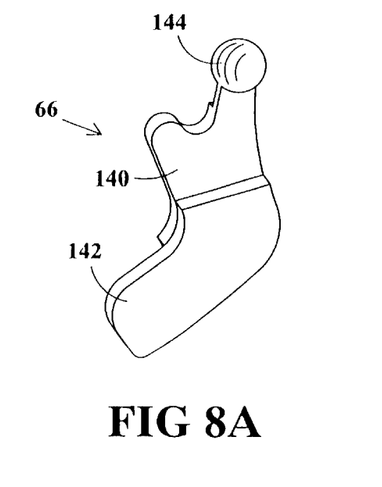
FIG. 8A is a side perspective view of the left mandibular ramus facsimile in the closed position of the oral surgery simulating device of the present invention.
Figure 9:
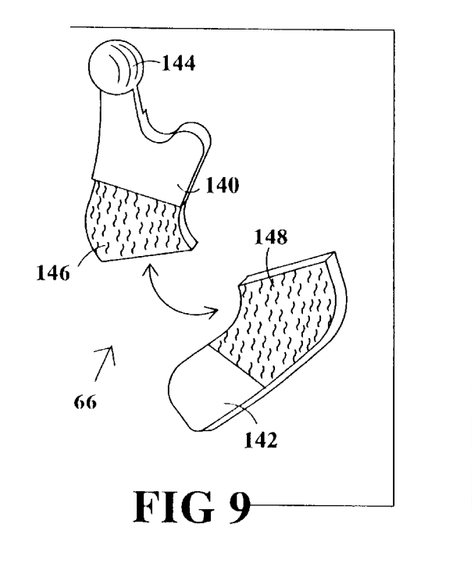
FIG. 9 is a side perspective view of the right mandibular ramus facsimile in the open position of the oral surgery simulating device of the present invention.
Figure 9A:
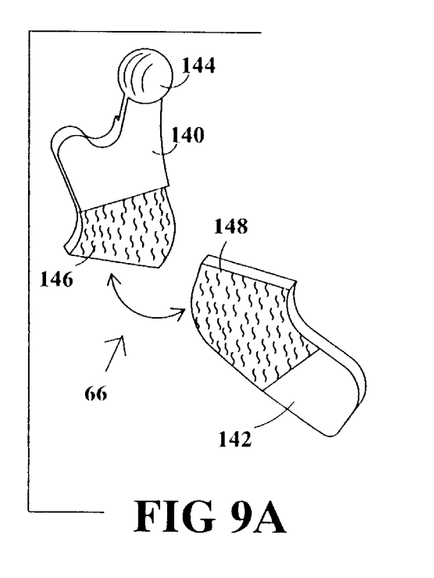
FIG. 9A is a side perspective view of the left mandibular ramus facsimile in the open position of the oral surgery simulating device of the present invention.

Pivotally connected to and extending from the stand 62 is the mandibular ramus facsimile 66. The mandibular ramus facsimile 66 is also illustrated in FIGS. 8, 8A, 9 and 9A. The pivotal connection of the mandibular ramus facsimile 66 to the stand is provided to mimic the movement of the ramus of the patient. The mandibular ramus facsimile 66 includes a first section 140, a second section 142 removably connected to the first section 140 and a pivotal connector 144 extending from the first section 140 in a side opposite the removable connection to the second section 142. The mandibular ramus facsimile 66 is illustrated in the closed position in which the first and second sections 140 and 142 are connected together in FIGS. 8 and 8A. The mandibular ramus facsimile 66 is illustrated in the open position in which the first and second sections 140 and 142 are separated from one another in FIGS. 9 and 9A. FIGS. 8 and 9 illustrate a right side mandibular ramus facsimile and FIGS. 8A and 9A illustrate a left side mandibular ramus facsimile. As can be seen from FIGS. 9 and 9A, the first section 140 includes a connection material 146 such as Velcro or a hook and loop fastener on a side opposite the pivotal connector 144 and the second section also includes a connection material 148 such as Velcro or a hook and loop fastener on a side to be releasably secured to the first section 140. When the mandibular ramus of the patient is measured, the first and second sections are secured whereby the size of the mandibular ramus facsimile is substantially similar to the size of the mandibular ramus of the patient.

Figure 4:
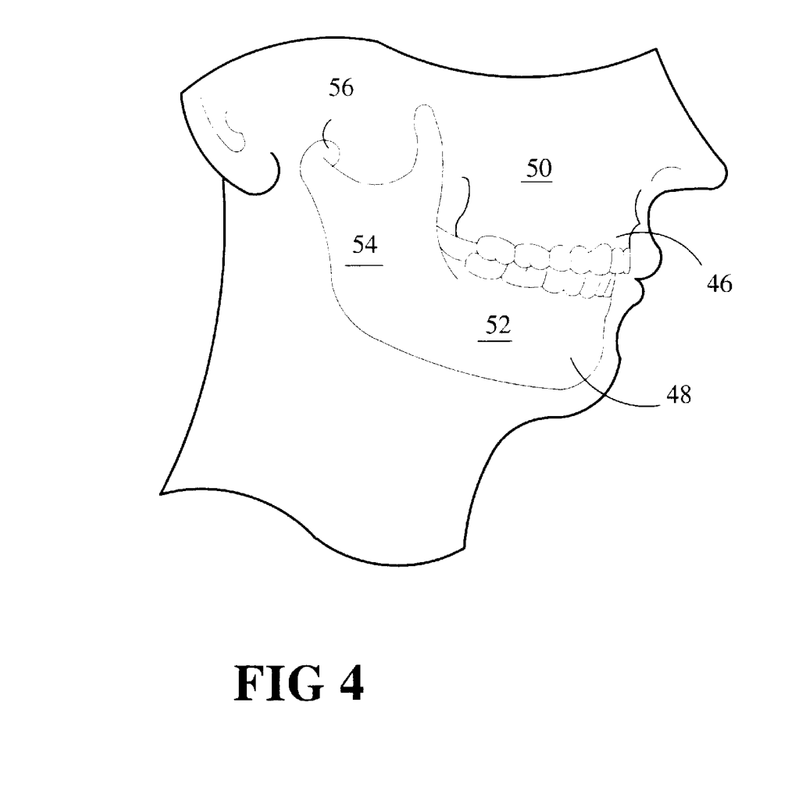
FIG. 4 is a side view of a mandibular ramus of a patient, the mandibular ramus requiring lengthening.
Figure 5:
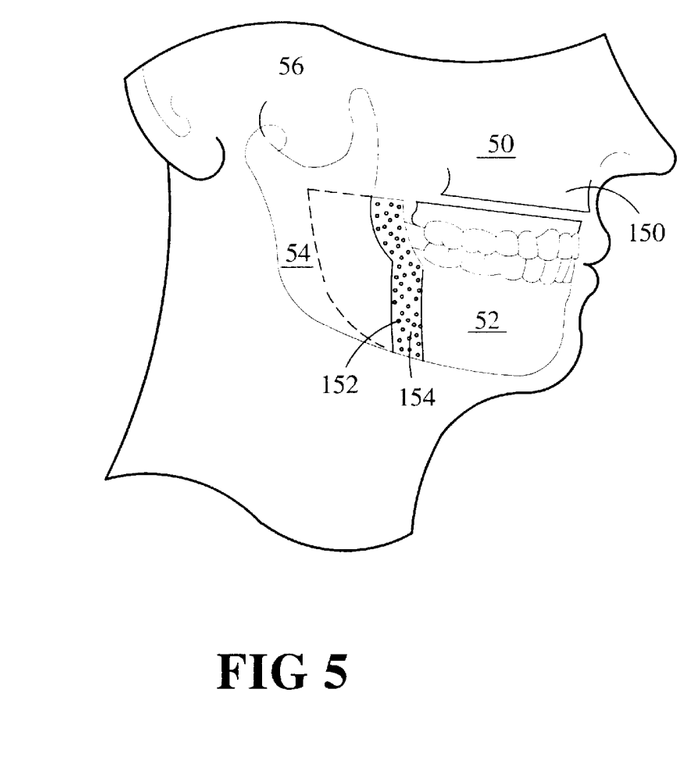
FIG. 5 is a side view of the mandibular ramus of FIG. 4 after being lengthened.

The operation of the oral surgery simulating device 10 will now be described with reference to the figures and specific reference to FIGS. 4 and 5 illustrating the upper and lower jaw of a person prior to and after surgery performed with the aid of the oral surgery simulating device 10 of the present invention. In operation, a cast of the upper and lower jaws of the patient are first produced. The pointer unit 114 is then positioned against the lower jaw of the patient and the first, second and third pointers 124, 126 and 130 are then adjusted to measure the lower jaw of the patient relative to Frankfurt's plane. The base side 116 of the pointer unit is then connected to the bottom side 118 of the base 58 of the oral surgery simulating device 10. The mandible unit 60 is then aligned with the pointer unit 114 by movement of the lateral rod 68 along the base and alignment of the adjustment device 74 such that the mandible plate is located directly below and positioned between the first, second and third pointers 124, 126 and 130. The cast of the mandible is now secured to the mandible plate 72.

The pointer unit 114 is now removed from its position connected to the base 58 and used to measure the maxilla of the patient. The pointers are positioned in contact with the maxilla of the patient and the first, second and third pointers 124, 126 and 130 are adjusted to provide a correct measurement. The pointer unit 114 is once again connected to the bottom side 118 of the base 58 at the same position at which the mandible was measured. The position of the maxilla plate 90 is now adjusted in the lateral and longitudinal directions. The knob 98 is used to adjust the maxilla plate 90 in the lateral direction and the knob 100 is used to adjust the maxilla plate 90 in the longitudinal direction. The adjustment device 96 is then adjusted to align the maxilla plate at the correct angle and positioned directly above the pointers of the pointer unit 114. The cast of the maxilla of the patient is now secured to the maxilla plate 90 by a securing substance such as glue. The position of the maxilla can thus be identified as it relates to Frankfurt's plane at all times.

The mandibular ramus of the patient is now measured and the mandibular ramus facsimile is adjusted to coincide with the measured values. This is done by securing the first and second sections 140 and 142 via the connecting substance 146 and 148 to form a mandibular ramus facsimile of the proper dimensions. The mandibular ramus facsimiles 66 are now pivotally connected to the stand 62. Additional measurements of the upper and lower jaws of the patient may now be taken and the positions of the mandible plate 72, the maxilla plate 90 and the mandibular rami 66 may be further adjusted. A substantially exact replica of the upper and lower jaws of the patient is now formed for the surgeon to study and form an operating plan from.

The replica is used by the surgeon to determine if procedures such as a sagittal split and LeFort I osteotomy is required. The upper and lower jaws of a patient in need of such procedures is illustrated in FIG. 4 while the results of such procedures are illustrated in FIG. 5. As can be seen from FIG. 4 the patient has a maxilla 50 which extends at an angle and also protrudes from the mouth past the mandible 52 to create a severe overbite. In order to correct the angle of the maxilla 50 a LeFort I osteotomy is required. During such a procedure, the maxilla 50 is broken to form a break 150 therein. The area formed between the bones of the maxilla is then filled in by a bone graft material in a manner which will align the maxilla to extend in a horizontal plane. In order to correct the overbite of the maxilla 50, a break 152 must be formed in the mandibular ramus 54. Such a break 152 is formed and the mandible 52 is then moved forward into alignment with the maxilla 50 to eliminate the overbite. The gap between the mandible 52 and the mandibular ramus 54 is filled by a naturally forming bone graft material. Such material is formed by the body and acts to reconnect the two bones.

Thus, by using the model formed with the present invention the surgeon is able to plan the entire procedure and determine at exactly what point the break in the bones needs to be formed. The surgeon is also able to determine how far the mandible must be moved to eliminate the overbite and how far the maxilla must be moved so it will extend horizontally.

From the above description it can be seen that the oral surgery simulating device of the present invention is able to overcome the shortcomings of prior art devices by providing an oral surgery simulating device which is able to produce a model of the maxilla and mandible accurately representing that of the patient and provide posterior, anterior, superior and inferior movement of the casts of the maxilla and mandible and rotation of the cast of the maxilla. The oral surgery simulating device includes a pointer device able to be adjusted for taking measurements of the maxilla and mandible relative to Frankfurt's horizontal plane and thus provide for accurate alignment of the casts of the maxilla and mandible and has a universal mandibular ramus facsimile for use in simulating a sagittal split of the mandibular ramus. The oral surgery simulating device is thus able to aid a surgeon in the planning of oral surgery and reduce the amount of time needed for preparation of the oral surgery by providing the surgeon with a more accurate plan regarding the necessary steps to perform during surgery. Furthermore, the oral surgery simulating device of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. An oral surgery simulating device for planning an oral surgery for a patient using a cast of the patients mandible and maxilla, said device comprising:

a) a stand including a base;

b) means for receiving the cast of the mandible of the patient movably connected to said base of said stand;

c) means for receiving the cast of the maxilla of the patient connected to said stand and positioned atop said cast of the mandible, said means for receiving the cast of the maxilla being adjustable in a lateral direction and rotatable about an axis; and    d) a pointing unit releasably connected to said stand for aligning the cast of the mandible and the cast of the maxilla with relation to Frankfort's horizontal plane to thereby provide a replica of an upper and lower jaw of the patient.

2. The oral surgery simulating device as recited in claim 1, wherein said pointer unit includes a pole, a C-shaped clamp connected to and slideable along a length of said pole, a first pointer extending from a midsection of said C-shaped clamp, a second pointer movably connected to a first leg of said C-shaped clamp and a third pointer movable connected to a second leg of said C-shaped clamp, said second and third pointers facing each other.

3. The oral surgery simulating device as recited in claim 2, wherein said first and second legs of said C-shaped clamp each being rotatably connected to said mid section.

4. The oral surgery simulating device as recited in claim 3, wherein said first and second legs of said C-shaped clamp being laterally displaceable with respect to said midsection.

5. The oral surgery simulating device as recited in claim 2, wherein said first and second legs of said C-shaped clamp being laterally displaceable with respect to said midsection.

6. The oral surgery simulating device as recited in claim 1, wherein said means for receiving the cast of the mandible includes a base section slideably connected to said base of said stand, a mandible plate for receiving the cast of the mandible and means for adjusting a position of said mandible plate connected between said base section and said mandible plate.

7. The oral surgery simulating device as recited in claim 6, wherein said means for adjusting the mandible plate includes a first adjuster connected to said base, a second adjuster connected to said mandible plate and a diagonal bar connected between said first and second adjusters.

8. The oral surgery simulating device as recited in claim 7, wherein said first adjuster includes a slot for receiving said diagonally extending bar, said diagonally extending bar being movable within said slot for pivoting said second adjuster and said mandible plate about said first adjuster.

9. The oral surgery simulating device as recited in claim 8, wherein said second adjuster is movable in a diagonal direction along a length of said diagonal bar.

10. The oral surgery simulating device as recited in claim 9, wherein said base section includes means for locking said means for receiving the cast of the mandible in a desired position on said base of said stand.

11. The oral surgery simulating device as recited in claim 1, wherein said means for receiving the cast of the maxilla includes a maxilla plate for receiving the cast of the maxilla, means for laterally adjusting said maxilla plate, means for longitudinally adjusting said maxilla plate and means for finely adjusting a position of said maxilla plate connected between said stand and said maxilla plate, said maxilla plate being positioned atop said mandible plate.

12. The oral surgery simulating device as recited in claim 11, wherein said means for finely adjusting said maxilla plate includes a third adjuster connected to said means for laterally adjusting, a fourth adjuster connected to said maxilla plate and a second diagonal bar connected between said third and fourth adjusters.

13. The oral surgery simulating device as recited in claim 12, wherein said third adjuster includes a slot receiving said second diagonal bar, said second diagonal bar being movable within said slot for pivoting said fourth adjuster and said maxilla plate about said third adjuster.

14. The oral surgery simulating device as recited in claim 13, wherein said fourth adjuster is movable in a diagonal direction along a length of said second diagonal bar.

15. The oral surgery simulating device as recited in claim 10, wherein said means for receiving the cast of the maxilla includes a maxilla plate for receiving the cast of the maxilla, means for laterally adjusting said maxilla plate, means for longitudinally adjusting said maxilla plate and means for finely adjusting a position of said maxilla plate connected between said stand and said maxilla plate, said maxilla plate being positioned atop said mandible plate.

16. The oral surgery simulating device as recited in claim 15, wherein said means for finely adjusting said maxilla plate includes a third adjuster connected to said means for laterally adjusting, a fourth adjuster connected to said maxilla plate and a second diagonal bar connected between said third and fourth adjusters.

17. The oral surgery simulating device as recited in claim 16, wherein said third adjuster includes a slot receiving said second diagonal bar, said second diagonal bar being movable within said slot for pivoting said fourth adjuster and said maxilla plate about said third adjuster.

18. The oral surgery simulating device as recited in claim 17, wherein said fourth adjuster is movable along a length of said second diagonal bar.

19. The oral surgery simulating device as recited in claim 1, further comprising a mandibular ramus facsimile pivotally connected to said stand for simulating a ramus of the patient.

20. The oral surgery simulating device as recited in claim 19, wherein said mandibular ramus includes a left and right mandibular ramus pivotally connected on either side of the mandibular plate.

21. The oral surgery simulating device as recited in claim 20, wherein said left and right mandibular ramus are each adjustable to match the left and right ramus of the patient.

22. An oral surgery simulating device for planning an oral surgery for a patient using a cast of the patients mandible and maxilla, said device comprising:
   a) a stand including a base;
   b) means for receiving the cast of the mandible of the patient movably connected to said base of said stand;
   c) means for receiving the cast of the maxilla of the patient connected to said stand and positioned atop said cast of the mandible, said means for receiving the cast of the maxilla being adjustable in a lateral direction and rotatable about an axis; and
   d) left and right mandibular ramus facsimiles, each pivotally connected to said stand on a respective side of said means for receiving the cast of the mandibular plate for simulating a lower jaw of the patient.

23. The oral surgery simulating device as recited in claim 22, further comprising a pointing unit releasably connected to said stand for aligning the cast of the mandible on the means for receiving the cast of the mandible and the cast of the maxilla on the means for receiving the cast of the maxilla with relation to Frankfort's horizontal plane to thereby provide a replica of an upper and lower jaw of the patient.

24. The oral surgery simulating device as recited in claim 23, wherein said pointer unit includes a pole, a C-shaped clamp connected to and slideable along a length of said pole, a first pointer extending from a midsection of said C-shaped clamp, a second pointer movably connected to a first leg of said C-shaped clamp and a third pointer movable connected to a second leg of said C-shaped clamp, said second and third pointers facing each other.

25. The oral surgery simulating device as recited in claim 24, wherein said first and second legs of said C-shaped clamp each being rotatably connected to said mid section.

26. The oral surgery simulating device as recited in claim 25, wherein said first and second legs of said C-shaped clamp being laterally displaceable with respect to said midsection.

27. The oral surgery simulating device as recited in claim 24, wherein said first and second legs of said C-shaped clamp are each laterally displaceable with respect to said midsection.

28. The oral surgery simulating device as recited in claim 22, wherein said means for receiving the cast of the mandible includes a base section slideably connected to said base of said stand, a mandible plate for receiving the cast of the mandible and means for adjusting a position of said mandible plate connected between said base section and said mandible plate.

29. The oral surgery simulating device as recited in claim 28, wherein said means for adjusting the mandible plate includes a first adjuster connected to said base, a second adjuster connected to said mandible plate and a diagonal bar connected between said first and second adjusters.

30. The oral surgery simulating device as recited in claim 29, wherein said first adjuster includes a slot for receiving said diagonally extending bar, said diagonally extending bar being movable within said slot for pivoting said second adjuster and said mandible plate about said first adjuster.

31. The oral surgery simulating device as recited in claim 30, wherein said second adjuster is movable in a diagonal direction along a length of said diagonal bar.

32. The oral surgery simulating device as recited in claim 31, wherein said base section includes means for locking said means for receiving the cast of the mandible in a desired position on said base of said stand.

33. The oral surgery simulating device as recited in claim 22, wherein said means for receiving the cast of the maxilla includes a maxilla plate for receiving the cast of the maxilla, means for laterally adjusting said maxilla plate, means for longitudinally adjusting said maxilla plate and means for finely adjusting a position of said maxilla plate connected between said stand and said maxilla plate, said maxilla plate being positioned atop said mandible plate.

34. The oral surgery simulating device as recited in claim 33, wherein said means for finely adjusting said maxilla plate includes a third adjuster connected to said means for laterally adjusting, a fourth adjuster connected to said maxilla plate and a second diagonal bar connected between said third and fourth adjusters.

35. The oral surgery simulating device as recited in claim 34, wherein said third adjuster includes a slot receiving said second diagonal bar, said second diagonal bar being movable within said slot for pivoting said fourth adjuster and said maxilla plate about said third adjuster.

36. The oral surgery simulating device as recited in claim 35, wherein said fourth adjuster is movable in a diagonal direction along a length of said second diagonal bar.

* * * * *